United States Patent
Lin et al.

(10) Patent No.: US 11,680,107 B2
(45) Date of Patent: Jun. 20, 2023

(54) HYDROGEL COMPOSITION FOR DRUG DELIVERY AND USES THEREOF

(71) Applicant: TAIPEI MEDICAL UNIVERSITY, Taipei (TW)

(72) Inventors: Shyr-Yi Lin, Taipei (TW); Ming-Thau Sheu, Taipei (TW); Kuo-Hsiang Chuang, Taipei (TW); Yi-Jou Chen, Taipei (TW); Pu-Sheng Wei, Taipei (TW)

(73) Assignee: Taipei Medical University, Taipei (TW)

( * ) Notice: Subject to any disclaimer, the term of this patent is extended or adjusted under 35 U.S.C. 154(b) by 110 days.

(21) Appl. No.: 16/825,612

(22) Filed: Mar. 20, 2020

(65) Prior Publication Data
US 2020/0299405 A1  Sep. 24, 2020

Related U.S. Application Data

(60) Provisional application No. 62/822,178, filed on Mar. 22, 2019.

(51) Int. Cl.
 - *C07K 16/30* (2006.01)
 - *A61K 9/06* (2006.01)
 - *A61K 47/34* (2017.01)
 - *C07K 16/28* (2006.01)

(52) U.S. Cl.
 CPC ............ *C07K 16/3076* (2013.01); *A61K 9/06* (2013.01); *A61K 47/34* (2013.01); *C07K 16/2809* (2013.01)

(58) Field of Classification Search
 CPC .. C07K 16/3076; C07K 16/2809; A61K 9/06; A61K 47/34; A61K 47/36; A61K 9/0024; A61K 39/39558; A61K 45/00; A61P 35/00

See application file for complete search history.

(56) References Cited

U.S. PATENT DOCUMENTS

| | | |
|---|---|---|
| 9,364,545 B2 | 6/2016 | Jhan et al. |
| 2013/0337045 A1 | 12/2013 | Bredehorst et al. |
| 2018/0256584 A1* | 9/2018 | Zale ..................... A61K 31/519 |

FOREIGN PATENT DOCUMENTS

| | | |
|---|---|---|
| EP | 2674167 A1 | 12/2013 |
| WO | 2018183984 A1 | 10/2018 |
| WO | 2019016233 A1 | 1/2019 |

OTHER PUBLICATIONS

R. Ahamadi-Fesharaki, et.al., "Design and Production of Bispecific Antibodies," Molecular Therapy: Oncolytics, 14(9), 2019:38-56.
Qiong Wang, et al., "Single-Chain Variable Fragment Based Bispecific Antibodies: Hitting Two Targets with One Sophisticated Arrow," Antibodies, 8, 43, 2019.

(Continued)

*Primary Examiner* — Gollamudi S Kishore
(74) *Attorney, Agent, or Firm* — Prosyla Group PC

(57) ABSTRACT

The present disclosure relates to a biodegradable and thermosensitive hydrogel composition comprising a diblock PLGA-PEG copolymer and a triblock PLGA-PEG-PLGA copolymer. A method for treating or alleviating one or more symptoms of a disease and a method for delivering an active agent are also provided.

24 Claims, 9 Drawing Sheets

(56) References Cited

OTHER PUBLICATIONS

Bonacucina, Giullia et al., "Thermosensitive Self-Assembling Block Copolymers as Drug Delivery Systems," Polymers, vol. 3, No. 4, pp. 779.811.
European Search Report issued in EP Patent Application No. 20164964.7 dated Jul. 31, 2020.
Qiao, M. et al., "Injectable biodegradable temperature-responsive PLGA-PEG-PLGA copolymers: Synthesis and effect of copolymer composition on drug release from the copolymer-based hydrogels," International Journal of Pharmaceutics, vol. 294,. No. 1-2, pp. 103-112.
Office Action issued in Taiwan Patent Application No. 109109681 dated Jun. 29, 2021.

\* cited by examiner

HYDROGEL COMPOSITION FOR DRUG DELIVERY AND USES THEREOF

This application claims the benefit and priority to U.S. Provisional Application No. 62/822,178, filed Mar. 22, 2019, entitled, "HYDROGEL FOR DRUG DELIVERY", the contents of which is disclosed herewith in its entirety.

FIELD OF THE DISCLOSURE

The present disclosure relates to a drug delivery; more particularly, to a hydrogel composition for drug delivery.

BACKGROUND OF THE DISCLOSURE

Drug delivery refers to approaches, formulations, technologies, and systems for transporting a pharmaceutical compound in the body as needed to safely achieve its desired therapeutic effect. An optimum material for use in a drug delivery device should be biodegradable, compatible with drugs, and allowed for fabrication with a simple in safe solvents, such as water. Moreover, the material preferably possesses a reverse thermal gelation property with a sol-gel transition temperature in a range of 25° C. to 35° C. The material with such thermal gelation property is able to maintain in a solution state when uniformly mixed with protein/polypeptide drugs at a temperature below room temperature and to transform to a gel structure following administration to a body site, with a sufficient structural integrity and gel strength to release the loaded drugs at a sustained manner. "Being biodegradable" means that a polymer used for the drug delivery can break down or degrade within the body to nontoxic components either concomitant with the drug release, or, after all drugs have been released. "Reverse thermal gelation property" means that a polymer has a sol-gel transition temperature when undergoing reverse thermal gelation. When the polymer is at a temperature below the sol-gel transition temperature, it is soluble in water; and when above, it undergoes phase transition to increase in viscosity or to form a semi-solid gel. "Structural integrity" means that the resultant gel body after transition from a sol state should maintain its original volume without any shrinkage of expelling water out of the gel body and leading to a burst release of the loaded drugs.

Hydrogels are being widely investigated for biomedical applications such as drug delivery and tissue engineering. Hydrogels are defined as three-dimensional physical or covalently cross-linked networks that are able to absorb a large amount of water while maintaining a semisolid morphology. The networks in hydrogels are able to retain a high level of water, making them very interesting candidates for carrying active ingredients and biomaterials. The hydrogel network can encapsulate and release therapeutics via various mechanisms, such as (de)swelling, external triggers, pH or temperature, erosion or diffusion. Hydrogel matrices moreover possess the ability to encapsulate and release therapeutics in a sustained manner over prolonged periods of time.

For example, BiTTAEs are classified into two groups of immunoglobulin G (IgG)-like and non-IgG-like molecules based on containing the Fc region or not. The IgG-like molecules, encompassing the Fc region, have effector functions (ADCC, ADCP, and CDC), easy purification, and a prolonged serum half-life due to their size above the renal clearance threshold and the neonatal Fc receptor (FcRn)-mediated recycling. The non-IgG-like molecules including tandem scFvs, diabody (single chain and tandem diabodies), dual-affinity retargeting molecules DARTs), Fab-scFv, etc., have a molecular weight in the range of 50-100 kDa. In view of being devoid of the Fc region, the non-IgG-like molecules have a short half-life due to their low molecular weight. Moreover, they benefit from superior tumor penetration, better epitope accessibility, less immunogenicity, and less complicated production compared with the IgG-like molecules. Those characteristics suggest those smaller formats of non-IgG-like BiTTAEs to be more advantageous for the treatment of solid tumors than regular mAbs, but with short plasma half-life leads to be necessary to frequent intravenous (iv) bolus administration or continuous iv infusion to maintain sustainable and effective plasma concentration (R. Ahamadi-Fesharaki, et. al., Molecular Therapy: Oncolytics, 14(9), 2019:38-56).

One of the most successful non-IgG like BiTTAE drugs (tandem scFv) is blinatumomab (Blincyto®), which has been approved by the FDA for the treatment of B-cell precursor acute lymphoblastic leukemia (ALL). Blinatumomab is comprised of an anti-CD 19 scFv in the VL-VH orientation linked through a short glycine/serine linker to an anti-CD3 scFv in the VH-VL orientation. Due to its small size, blinatumomab can reach in close proximity to T-cell and target cell membranes, but this feature also leads to the rapid clearance from circulation with a short elimination half-life (mean±SD) of 1.25±0.63 h, which is presumed to be eliminated renally. As a result, BiTTAE requires continuous dosing at a high concentration (15-28 mcg per day) to recruit and activate a large amount of suboptimal T cells to achieve half-maximal target cell lysis. Therefore, this antibody is administered as a 4-week continuous iv infusion to maintain sufficient therapeutic serum concentration, which increases costs by having to produce more clinical-grade antibodies. On the other hand, the single polypeptide chain structure that enhances non-IgG-like BiTTAE antibody-antigen recognition, however, comes at the cost of increased aggregation and decreasing protein stability (Qiong Wang, et al., Antibodies, 8, 43, 2019).

Several copolymers are utilized as the hydrogels for drug delivery. However, none of the conventional copolymers meet the requirements of being biodegradable, reverse thermal gelation property, and structural integrity.

There is a need to develop a hydrogel for slow-release of a biologic so that the biologic can be effectively delivered to a subject. Furthermore, it would be highly desirable to develop an injectable or implantable polymeric drug delivery system for the delivery of short serum half-life drugs in particular, at a controlled rate over a sustained period of time, to optimize the therapeutic efficacy, minimize the side effects and toxicity, and thereby to increase the efficacy and patient compliance.

SUMMARY OF THE DISCLOSURE

A thermosensitive and biodegradable hydrogel composition is provided in the disclosure with improved slow-release ability to an active agent, especially to a protein drug.

The present disclosure provides a composition comprising a hydrogel containing:

a diblock PLGA-PEG copolymer comprising a poly(ethylene glycol) (PEG) segment and a poly(lactide-co-glycolide) (PLGA) segment, the PEG segment having a weight averaged molecular weight ($_wMW$) of from about 400 Da to about 1,000 Da, the PLGA segment having a $_wMW$ of from about 900 Da to about 1800 Da, wherein the ratio of the PEG segment to the PLGA segment is from about 1/1.5 to about 1/3.0, and a total $_wMW$ of the diblock PLGA-PEG copolymer is from about 1,000 Da to about 3,000; and a triblock PLGA-PEG-PLGA copolymer comprising a PEG segment and a PLGA segment, the PEG segment having a $_wMW$ of about 800 Da to about 1,600 Da, the PLGA segment having a $_wMW$ of about 1,000 Da to about 1,500 Da, wherein the ratio of the PEG segment to the PLGA segment is from about 1/1.5 to about 1/3.0, and a total $_wMW$ of the triblock PLGA-PEG-PLGA copolymer is from about 3,000 Da to about 5,000 Da; and wherein the ratio of the diblock PLGA-PEG copolymer to the triblock PLGA-PEG-PLGA copolymer is from about 1/9 to about 9/1.

The present disclosure provides a method for delivering an active agent comprising loading the active agent with the composition as mentioned above.

In one preferred embodiment of the disclosure, the method for delivering the active agent as mentioned above further comprises a step of administrating the hydrogel to a subject, wherein the step is selected from the group consisting of: intratumoral injection, subcutaneous injection, peritumoral injection, injection of a resultant cavity of tumor resection, oral delivery, ocular delivery, transdermal, ophthalmic, wound healing, intraperitoneal injection, gene delivery, tissue engineering, colon specific drug delivery.

The present disclosure provides a method for treating or alleviating one or more symptoms of a disease in a subject, comprising administering to the subject the composition as mentioned above.

The present disclosure is described in detail in the following sections. Other characteristics, purposes and advantages of the present disclosure can be found in the detailed description and claims.

DETAILED DESCRIPTION OF THE DISCLOSURE

Figure 1:
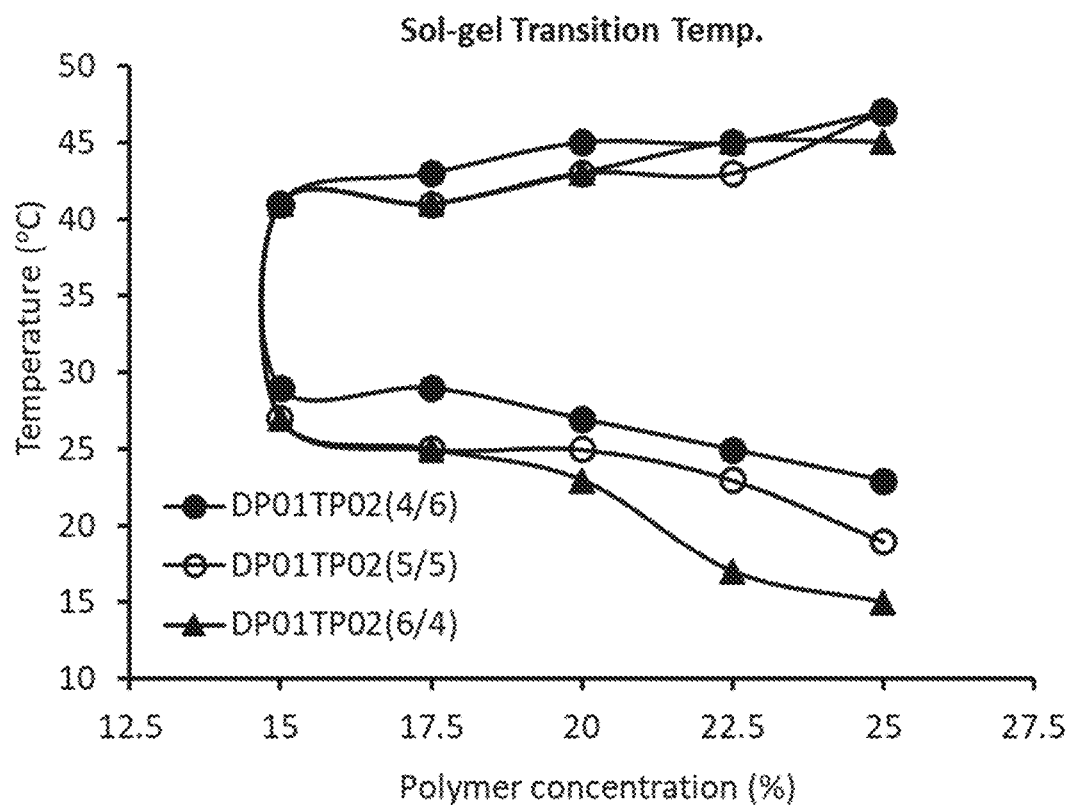
FIG. 1 is a graphical representation of a phase of diblock PLGA-PEG copolymer and triblock PLGA-PEG-PLGA copolymer aqueous solutions.

The present disclosure can be more readily understood by reference to the following detailed description of various embodiments of the disclosure, the examples, and the chemical drawings and tables with their relevant descriptions. It is to be understood that unless otherwise specifically indicated by the claims, the disclosure is not limited to specific preparation methods, carriers or formulations, or to particular modes of formulating the extract of the disclosure into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "polymer" as used herein is defined as a large molecule comprising a linear arrangement of simpler repeating subunits. The term "copolymer" as used herein refers to a polymer derived from more than one species of monomer.

The term "hydrogel" as used herein refers to a three-dimensional, hydrophilic or amphiphilic polymeric network capable of taking up large quantities of water. The networks are composed of homopolymers or copolymers, and are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media.

The term "temperature sensitive" hydrogel as used herein refers to a block copolymer of the present disclosure and forms, to various degrees, a jelly-like or gelled product when heated to a particular temperature, for example body temperature (37° C.), or a temperature higher than about 25° C. The block copolymer is preferably a liquid at room temperature and soluble in water, but upon reaching a particular temperature, forms a hydrogel when mixed with water such that water is a dispersion medium forming the hydrogel.

The term "active agent" is used herein to refer to a chemical material or compound suitable for administration to a human patient and that induces a desired beneficial effect, e.g., exhibits a desired pharmacological activity. The term includes, for example, agents that are therapeutically effective, prophylactically effective, and cosmetically (and cosmeceutically) effective. Also included are derivatives and analogs of those compounds or classes of compounds specifically mentioned which also induce the desired beneficial effect.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "being biodegradable" means that a substance can break down or degrade within an organism to nontoxic components either concomitant with an active agent release, or, after all active agent have been released.

The term "reverse thermal gelation property" means that a polymer has a sol-gel transition temperature when undergoing reverse thermal gelation. When the polymer is at a temperature below the sol-gel transition temperature, it is soluble in water; and when above, it undergoes phase transition to increase in viscosity or to form a semi-solid gel.

The term "structural integrity" means that a resultant gel body after transition from a sol state should maintain its original volume without any shrinkage of expelling solvent out of the gel body and leading to a burst release of loaded active agents.

It is to be observed that there has been no previous disclosures of a biodegradable and thermosensitive composition comprising diblock PLGA-PEG and triblock PLGA-PEG-PLGA possessing a reverse thermal gelation property with a sol-gel transition temperature in a proper range and the resultant gel having a structural integrity with a gel strength high enough to release an active agent such as non-IgG like BiTTAEs at a sustained manner. It has been unexpectedly demonstrated that a thermosensitive and biodegradable hydrogel composition that maintains in a liquid state at room temperature for being uniformly mixed with an active agent and transforms into a gel form with structural integrity having an enough gel strength to release the active agent in a sustained manner without burst effect at body temperature after subcutaneous or in situ tumor site injection. It has been unexpectedly demonstrated that composition comprising the diblock PLGA-PEG copolymer and the triblock PLGA-PEG-PLGA copolymer is more effective to have a sol-gel transition temperature in a range of about 25° C. to about 35° C. and the resultant gel with a structural integrity that could release loaded the active agent such as non-IgG like BiTTAEs in a sustained manner without burst effect. Controlling the molecular weights, compositions, and relative ratios of the hydrophilic PEG segment and hydrophobic PLGA segment of the diblock PLGA-PEG copolymer and the triblock PLGA-PEG-PLGA copolymer, and the relative amounts of diblock PLGA-PEG copolymer and triblock PLGA-PEG-PLGA copolymer can optimize desirable properties.

The present disclosure provides a composition comprising a hydrogel containing:
   a diblock PLGA-PEG copolymer comprising a poly(ethylene glycol) (PEG) segment and a poly(lactide-co-glycolide) (PLGA) segment, the PEG segment having a weight averaged molecular weight ($_wMW$) of from about 400 Da to about 1,000 Da, the PLGA segment having a $_wMW$ of from about 900 Da to about 1800 Da, wherein the ratio of the PEG segment to the PLGA segment is from about 1/1.5 to about 1/3.0, and a total $_wMW$ of the diblock PLGA-PEG copolymer is from about 1,000 Da to about 3,000; and
   a triblock PLGA-PEG-PLGA copolymer comprising a PEG segment and a PLGA segment, the PEG segment having a $_wMW$ of about 800 Da to about 1,600 Da, the PLGA segment having a $_wMW$ of about 1,000 Da to about 1,500 Da, wherein the ratio of the PEG segment to the PLGA segment is from about 1/1.5 to about 1/3.0, and a total $_wMW$ of the triblock PLGA-PEG-PLGA copolymer is from about 3,000 Da to about 5,000 Da; and
   wherein the ratio of the diblock PLGA-PEG copolymer to the triblock PLGA-PEG-PLGA copolymer is from about 1/9 to about 9/1.

According to the disclosure, lactide is the lactone cyclic di-ester derived from lactic acid (2-hydroxypropionic acid) with the formula $(OCHCO_2)_2$. Lactide according to the disclosure includes all stereoisomeric forms. Lactide can be polymerized to polylactic acid (polylactide) or copolymerized with other monomers. The lactide block according to the disclosure refers to a subunit polymerized from a lactide monomer in the copolymer.

According to the disclosure, glycolide is a cyclic dimer of $\alpha$-hydroxy acid that can be used in the formation of aliphatic polyester. The formula of glycolide is $C_4H_4O_4$. Glycolide can be polymerized to polyglycolide or copolymerized with other monomers. The glycolide block according to the disclosure refers to a subunit polymerized from a glycolide monomer in the copolymer.

According to the disclosure, poly(ethylene glycol), also known as polyethylene glycol and PEG, is a polyether compound with the formula $R-(O-CH_2-CH_2)_n-OH$, wherein R is H or $C_{1-3}$ alkyl. Poly(ethylene glycol) is also referred to as polyethylene oxide (PEO) or polyoxyethylene (POE), depending on its molecular weight. Poly(ethylene glycol) can be copolymerized with other monomers or copolymers. The poly(ethylene glycol) segment according to the disclosure refers to a subunit in the copolymer.

In one embodiment of the disclosure, the poly(ethylene glycol) segment is a methoxy poly(ethylene glycol) segment with the formula $CH_3-(O-CH_2-CH_2)_n-$.

All compositions of the copolymer according to the disclosure are non-toxic, biodegradable and non-irritating. In one embodiment of the disclosure, the copolymer comprises a poly(ethylene glycol) segment and a poly(lactide-co-glycolide) segment. The poly(lactide-co-glycolide) block, also known as PLGA or PLG, has excellent biodegradability and biocompatibility. The poly(lactide-co-glycolide) segment is synthesized preferably by means of ring-opening co-polymerization of glycolic acid and lactic acid. According to the disclosure, the poly(lactide-co-glycolide) segment can be synthesized as either random or block copolymers, thereby imparting additional polymer properties. During polymerization, successive monomeric units are linked together in the poly(lactide-co-glycolide) segment by ester linkages, thus yielding a linear, aliphatic polyester. Depending on the ratio of lactide to glycolide used for the polymerization, different forms of the poly(lactide-co-glycolide) segment can be obtained.

In one embodiment of the disclosure, the diblock PLGA-PEG copolymer comprising a poly(ethylene glycol) segment and a poly(lactide-co-glycolide) segment has a structure of methoxy poly(ethylene glycol) segment-poly(lactide-co-glycolide) segment (mPEG-PLGA), referred to as Polymer C shown in Scheme 1.

In one embodiment of the disclosure, triblock PLGA-PEG-PLGA copolymer comprising a PEG segment and a PLGA segment, the PEG segment has a structure of poly(lactide-co-glycolide) segment-poly(ethylene glycol) segment-poly(lactide-co-glycolide) segment (PLGA-PEG-PLGA), referred to as Polymer B shown in Scheme 1.

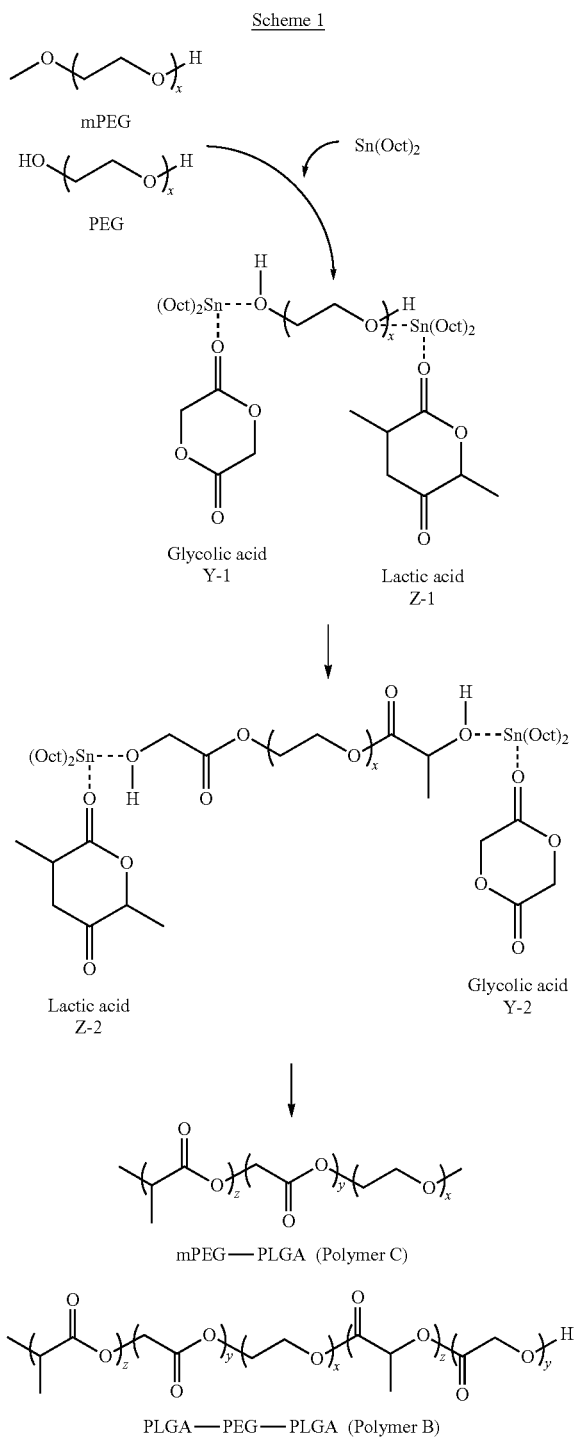

According to the disclosure, the diblock PLGA-PEG copolymer comprises the PEG segment and the PLGA segment, the PEG segment having a $_wMW$ of from about 400 Da to about 1,000 Da, the PLGA segment having a $_wMW$ of from about 900 Da to about 1800 Da, wherein the ratio of the PEG segment to the PLGA segment is from about 1/1.5 to about 1/3.0, and a total $_wMW$ of the diblock PLGA-PEG copolymer is from about 1,000 Da to about 3,000.

In one preferred embodiment of the disclosure, the diblock PLGA-PEG copolymer comprises the PEG segment having a $_wMW$ of from about 400 Da to about 900 Da, the PLGA segment having a $_wMW$ of from about 900 Da to about 1,800 Da, wherein the ratio of the PEG segment to the PLGA segment is from about 1/1.6 to about 1/2.6, and a total $_wMW$ of the diblock PLGA-PEG copolymer is from about 1,300 Da to about 2,500.

In one more preferred embodiment of the disclosure, the diblock PLGA-PEG copolymer comprises the PEG segment having a $_wMW$ of from about 550 Da to about 750 Da, the PLGA segment having a $_wMW$ of from about 900 Da to about 1,800 Da, wherein the ratio of the PEG segment to the PLGA segment is from about 1/1.6 to about 1/2.6, and a total $_wMW$ of the diblock PLGA-PEG copolymer is from about 1,300 Da to about 2,500.

In one still more preferred embodiment of the disclosure, the diblock PLGA-PEG copolymer comprises the PEG segment having a $_wMW$ of about 550 Da and the PLGA segment having a $_wMW$ of about 1,400 Da, the ratio of the PEG segment to the PLGA segment is from about 1/2.6, and a total $_wMW$ of the diblock PLGA-PEG copolymer is about 2,000 Da.

According to the disclosure, the triblock PLGA-PEG-PLGA copolymer comprises the PEG segment and the PLGA segment, the PEG segment having a $_wMW$ of about 800 Da to about 1,600 Da, the PLGA segment having a $_wMW$ of about 1,000 Da to about 1,500 Da, wherein the ratio of the PEG segment to the PLGA segment is from about 1/1.5 to about 1/3.0, and a total $_wMW$ of the triblock PLGA-PEG-PLGA copolymer is from about 3,000 Da to about 5,000 Da.

In one preferred embodiment of the disclosure, the triblock PLGA-PEG-PLGA copolymer comprises the PEG segment having a $_wMW$ of from about 800 Da to about 1,600 Da, the PLGA segment having a $_wMW$ of from about 1,200 Da to about 1,400 Da, wherein the ratio of the PEG segment to the PLGA segment is from about 1/1.6 to about 1/2.6, and a total $_wMW$ of the triblock PLGA-PEG-PLGA copolymer is from about 3,500 Da to about 4,500.

In one more preferred embodiment of the disclosure, the triblock PLGA-PEG-PLGA copolymer comprises the PEG segment having a $_wMW$ of from about 1,000 Da to about 1,500 Da, the PLGA segment having a $_wMW$ of from about 1,200 Da to about 1,400 Da, wherein the ratio of the PEG segment to the PLGA segment is from about 1/1.6 to about 1/2.6, and a total $_wMW$ of the triblock PLGA-PEG-PLGA copolymer is from about 3,500 Da to about 4,500.

In one still more preferred embodiment of the disclosure, the triblock PLGA-PEG-PLGA copolymer comprises the PEG segment having a $_wMW$ of about 1,500 Da and the PLGA segment having a $_wMW$ of about 1,450 Da, the ratio of the PEG segment to the PLGA segment is from about 1/1.6, and a total $_wMW$ of the triblock PLGA-PEG-PLGA copolymer is about 4,400 Da.

According to the disclosure, the ratio of the diblock PLGA-PEG copolymer to the triblock PLGA-PEG-PLGA copolymer is from about 1/9 to about 9/1; preferably, about 1/2 to about 2/1; more preferably from about 4/6 to about 6/4; still more preferably is 5/5 or 4/6.

The hydrogel according to the disclosure is biodegradable and thermosensitive, possessing a reverse thermal gelation property. The hydrogel according to the disclosure has a structural integrity without shrinkage.

In one embodiment of the disclosure, a sol-gel transition temperature of the hydrogel is from about 25° C. to about 35° C. The hydrogel according to the disclosure is in solution at room temperature or lower and gel at or about body temperature to achieve a uniformly mixing with an active agent. It is believed, though not intended to be restricted by theory, that the hydrogel according to the disclosure is in a liquid form at room temperature, and such property benefits manipulation. When administrated into a subject, the hydrogel according to the disclosure is in a gel form, and such property benefits slow release of an active agent.

In one preferred embodiment of the disclosure, the composition further comprises additives such as a salt or a buffer. Examples of the salt include but are not limited to about 0.137 M to about 0.450 M of NaCl, about 0.0027 M to about 0.0081 M of KCl, about 0.01 M to about 0.03 M of $Na_2HPO_4$, and about 0.0018 M to about 0.0054 M of $KH_2PO_4$. Examples of the buffer include but are not limited to about 0.02 M to about 0.06 M of Tris-HCl.

The content of the hydrogel in the composition varies according to application. In one preferred embodiment of the disclosure, the composition comprises about 10 wt % to about 20 wt % of the hydrogel; preferably about 12 wt % to about 18 wt %; more preferably about 14 wt % to about 16 wt %.

The composition also include any pharmaceutically active agent useful in treating physiological conditions. The active agent can be any substance that can be released from the composition to treat an undesirable physiological condition. The indication to be treated determines the active agent to be administered. The active agent includes, but is not limited to, an antigen, an antibody or fragments thereof, a wound hearing agent, an anticancer drug, a radionuclide, a gene therapy composition, a hormone, a nutriceutical, an antibiotic, an anti-inflammatory agent, an anti-viral agent, an antibacterial agent and a combination thereof. In one embodiment, the present disclosure provides localized deposition of a large variety of substances, that if administered by, for example, intravenous methods would cause undesirable systemic effects. This is particularly the case where the substances are toxic in some respect, and the toxicity is to be used for local treatment at a specific trauma site in the body. A typical example would be toxins for the treatment of, for example, cancer tumors. Particular examples of antibiotics include an antibiotic selected from the group consisting of tetracycline, minocycline, doxycycline, ofloxacin, revofloxacin, ciprofloxacin, clarithromycin, erythromycin, cefaclor, cefotaxim, imipenem, penicillin, gentamycin, streptomycin, bancomycin, or a derivative or mixture thereof. Particular examples of anti-cancer agents include methotrexate, carboplatin, taxol, cisplatin, 5-fluorouracil, doxorubicin, etpocide, paclitaxel, docetaxel, camtotecin, cytosine, arabinose, and derivatives and mixtures thereof. Particular examples of anti-inflammatory agents include an anti-inflammatory agent selected from the group consisting of indometacin, ibuprofen, ketoprofen, piroxicam, flubiprofen, diclofenac, and derivatives and mixtures thereof. Particular examples of anti-viral agents include an anti-viral agent selected from the group consisting of acyclovir, robavin, and derivatives and mixtures thereof. Particular examples of antibacterial agents include an antibacterial agent selected from the group consisting of ketoconazole, itraconazole, fluconazole, amphotericin-B, griceofulvin, and derivatives and mixtures thereof.

In one preferred embodiment of the disclosure, the active agent is a bispecific T cell/tumor associated antigen engager (BiTTAE); more preferably, is non-IgG-like BiTTAEs.

In one preferred embodiment of the disclosure, the non-IgG like bispecific T cell/Tumor associated antigen engager comprises a first antigen-binding domain that binds CD3, a second antigen-binding domain that binds human cancer with over-expressing tumor associated antigen, and wherein a molecular weight of the BiTTAE is from about 50 kDa to about 100 kDa. Preferably, the over-expressing tumor associated antigen in non-IgG like BiTTAEs is EGFR, PSMA, HER2, or EpiCam. In another aspect, the second antigen-binding domain is preferably a construct of tandem scFvs, single chain and tandem diabodies (diabody), dual-affinity retargeting molecules (DARTs), or Fab-scFv.

In one preferred embodiment of the disclosure, the active agent is a protein, more preferably an antibody. Preferably, the composition according to the disclosure further comprises a stabilizer. Examples of the stabilizer include but are not limited to citric acid, lysine monohydrochloride, Tween 80, and trehalose dihydrate.

The composition of the disclosure has significant anti-cancer activity against cancer cells. Intratumoral administration of the composition results in efficient growth inhibition of cancer cells. The tumor inhibition rate of the composition is significantly higher than that of anti-cancer agent only. The in situ injectable hydrogel of the invention is a drug delivery system that could increase the efficacy of cancer chemotherapy.

The composition according to the present disclosure effectively delivers the active agent in a sustained manner in the subject. Furthermore, the active agent is administered at physiologically relevant temperatures (temperatures <45° C.) to a subcutaneous area, tumor site, peritumor site, or resultant cavity after tumor resection.

In another aspect, the composition according to the disclosure eliminates the need for surgical procedure and offers the ability to form any desired implant shape.

In still another aspect, the composition according to the disclosure is stimuli sensitive and organic solvent-free injectable.

In still another aspect, the composition according to the disclosure exhibits low viscosity at formulation stage and gels quickly at body conditions.

The present disclosure provides a method for delivering an active agent comprising loading the active agent with the composition as mentioned above.

In one preferred embodiment of the disclosure, the method as mentioned above further comprises a step of administrating the hydrogel to a subject, wherein the step is selected from the group consisting of: intratumoral injection, peritumoral injection, injection of a resultant cavity of tumor resection, subcutaneous injection, oral delivery, ocular delivery, transdermal, ophthalmic, wound healing, intraperitoneal injection, gene delivery, tissue engineering, colon specific drug delivery.

The composition according to the disclosure is easily injected subcutaneously, intramuscularly, intratumorly, peritumorly, or into the resultant cavity of tumor resection. Furthermore, the composition allows to instantly form a gel body with less extent of shrinkage after subcutaneous, intramuscular, intratumor, or peritumor injection or injection into the resultant cavity of tumor resection.

In another aspect, the composition according to the disclosure allows to instantly form a gel body with less extent of shrinkage after subcutaneous, intramuscular, intratumor, or peritumor injection or injection into the resultant cavity of tumor resection to release loaded drugs at a desirable rate without an initial burst effect.

The present disclosure provides a method for treating or alleviating one or more symptoms of a disease a subject in a subject, comprising administering to the subject the composition as mentioned above.

The composition can be administered in liquid state, such as by injection, to a subject in need of therapy. Polymerization can be induced (initiated) either before or after administration, whereby the composition can be in a gel form. In one embodiment of the disclosure, a method of administering a composition to provide therapy to a site in need thereof includes providing a gel-forming composition as described, administering said gel-forming composition to the site, and initiating polymerization of said gel-forming composition by body temperature to form a gel.

Preferably, the disease is a cancer or wound.

The following examples are provided to aid those skilled in the art in practicing the present disclosure.

Examples

Preparation of mPEG-PLGA (550-1400)

Methoxy poly(ethylene glycol)-poly(lactide-co-glycolide) (mPEG-PLGA) diblock copolymers comprising about 50% to about 65% lactide, about 8% to about 12% glycolide, and about 25% to about 45% polyethylene glycol, was synthesized by typical ring-opening polymerization of lactide and glycolide using mPEG as initiator. First, mPEG was dried in a flask under vacuum at 120° C. for 1 h. Next, amounts of lactide and glycolide were added to the dried mPEG in the flask to receive the original reactant. Tin(II) 2-ethylhexanoate was subsequently added to the system as catalyst and the system was heated and maintained at 160° C. for 8 hours with nitrogen protection.

The resulting copolymers were dissolved in water and the solutions were heated at 80° C. to precipitate the copolymer. After three times of preceding steps to remove the unreacted monomers, the purified copolymers were following lyophilized and stored at −80° C. The molecular weights of copolymers were determined with $^1$H-NMR spectrometer (500 Hz), and the results are shown in Table 1.

TABLE 1

| Copolymer | Name | Ratio of PEG/PLGA | Mn |
|---|---|---|---|
| mPEG-PLGA (550-1400) | DP01 | 1/2.6 | 2000 |
| mPEG-PLGA (550-900) | DP02 | 1/1.6 | 1300 |
| mPEG-PLGA (750-1800) | DP03 | 1/2.4 | 2500 |
| mPEG-PLGA (750-1200) | DP04 | 1/1.6 | 1900 |

Preparation of PLGA-PEG-PLGA (1250-1500-1250)

Poly(lactide-co-glycolide)-poly(ethylene glycol)-poly(lactide-co-glycolide) (PLGA-PEG-PLGA) triblock copolymers, were synthesized by typical ring-opening polymerization of lactide and glycolide using PEG as initiator. First, PEG was dried in a flask under vacuum at 120° C. for 1 h. Next, amounts of lactide and glycolide were added to the dried PEG in the flask to receive the original reactant. Tin(II) 2-ethylhexanoate was then added to the system as the catalyst and the system was heated and maintained at 160° C. for 8 hours with nitrogen protection. The resulting copolymers were dissolved in water and the solution was heated at 80° C. to precipitate the copolymer. After the preceding steps were done three times to remove the unreacted monomers, the purified copolymers were lyophilized and stored at −80° C. The molecular weight of copolymers was determined with $^1$H-NMR spectrometer (500 Hz), and the results are shown in Table 2.

TABLE 2

| Copolymer | Name | Ratio of PEG/PLGA | Mn |
|---|---|---|---|
| PLGA-PEG-PLGA (1300-1000-1300) | TP01 | 1/2.6 | 3500 |
| PLGA-PEG-PLGA (1250-1500-1250) | TP02 | 1/1.6 | 4200 |
| PLGA-PEG-PLGA (800-1000-800) | TP03 | 1/1.6 | 2650 |

Determination of Sol-Gel Transition Temperature

Diblock mPEG-PLGA and triblock PLGA-PEG-PLGA were dissolved in PBS or TBS to form a polymer solution. First, each hydrogel with different diblock/triblock ratio was prepared and stored at 4° C. Then, each sample was incubated in water bath from 10° C. with heating rate of 1° C./1 min to obtain the gelatin temperature of each formulation. Finally, these formulations were placed at 4° C. for 24 hours for shrinkage ratio measurement. In addition, 0.1 mL of the hydrogel was placed onto the rheometer (MCR 302, Anton Paar) and the rheology property was observed at 37° C. to estimate the storage modulus (G'). The results are shown in Table 3 and Table 4.

TABLE 3

| Gel or Mix gel (15%) | Gelatin temperature (° C.) | Shrinkage ratio at 37° C. | G' at 37° C. |
|---|---|---|---|
| TP01 | 10 | 80% | N/A |
| DP01 | 15 | 75% | N/A |
| DP03 | 31 | 0% | 70 (PBS) |
| DP01TP02(5/5) | 28 | 12.5% | 65 (PBS) 75 (TBS) |
| DP01TP02(4/6) | 31 | 0% | 97 (PBS) 107 (TBS) |
| DP01DP02(5/5) | 16 | 50% | N/A |
| DP02TP03(5/5) | 19 | 60% | N/A |
| DP03TP03(5/5) | 23 | 20% | N/A |
| DP04TP01(5/5) | 27 | 0% | 24 (PBS) |

TABLE 4

| Gel or Mix gel (20%) | Gelatin temperature (° C.) | Shrinkage ratio at 37° C. | G' at 37° C. |
|---|---|---|---|
| DP01TP02(5/5) | 25 | 0% | 86 (PBS) |
| DP01TP02(4/6) | 27 | 0% | 62 (PBS) |
| DP02TP03(5/5) | 17 | 50% | N/A |
| DP03TP03(5/5) | 23 | 10% | N/A |
| DP04TP01(5/5) | 23 | 0% | 46 (PBS) |

Determination of Sol-Gel Transition Temperature

DP01 and TP02 were dissolved in PBS to form polymer solutions. The solutions of different ratios of DP01 and TP02 copolymers were prepared with a concentration range of 15% to 25%. Three ratios of DP01/TP02 (6/4, 5/5, 4/6) were used in the sol-gel transition experiment. First, each hydrogel with different concentrations was prepared and stored at 4° C. Then, each sample was incubated in water bath from 15° C. to 45° C. with heating rate of 1° C./1 min. The phase transition temperature was identified when the solution stopped flowing under shaking. The results are shown in FIG. 1.

Rheology of Hydrogel

Figure 2:
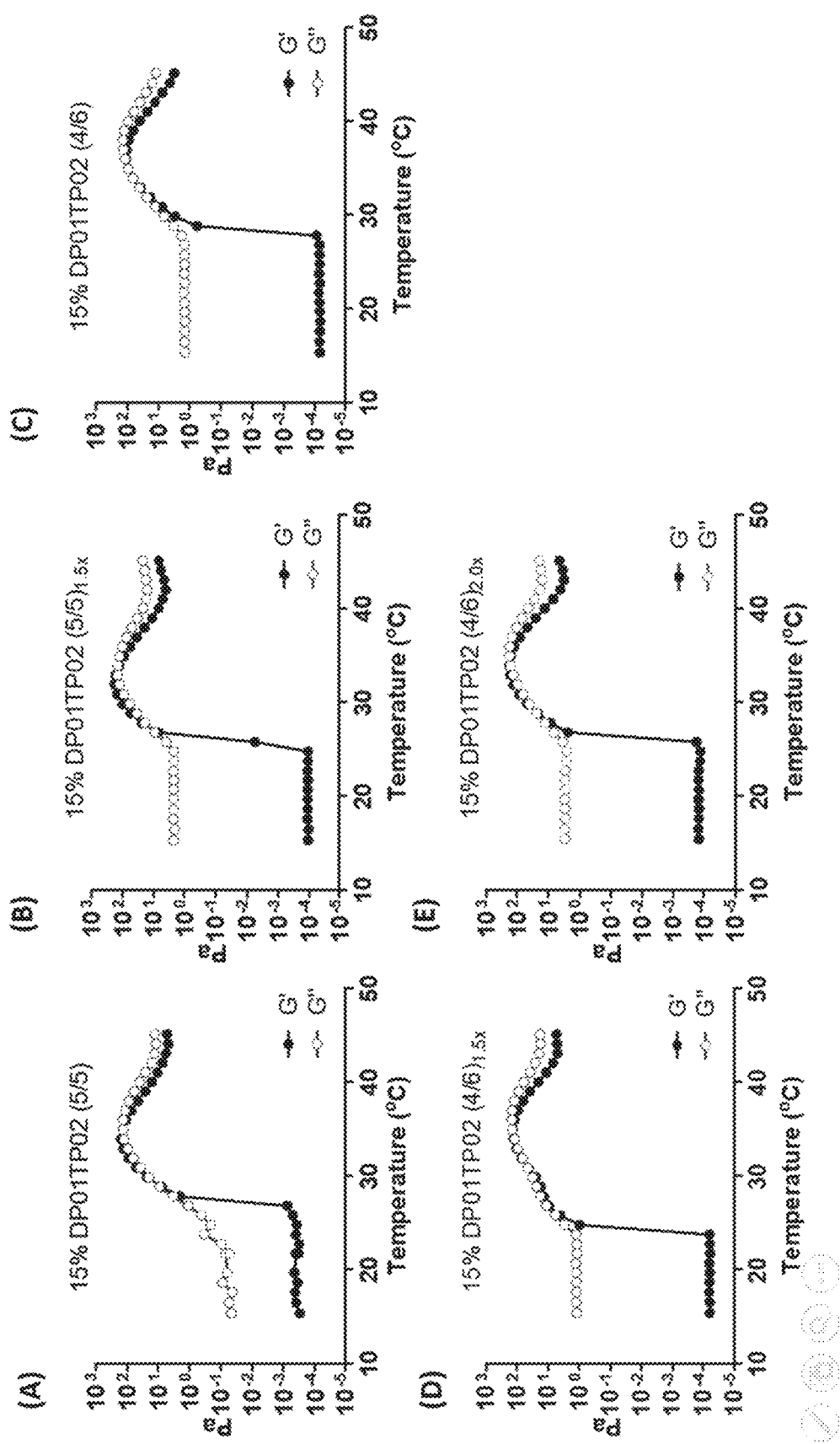
FIG. 2 is a representation of elastic modulus (G') and storage modulus (G") of 15 wt % of diblock PLGA-PEG copolymer and triblock PLGA-PEG-PLGA copolymer aqueous solutions as a function of temperature.

A 15% hydrogel was prepared according to the description in Table 5. 0.1 mL of the hydrogel was placed onto the rheometer (MCR 102, Anton Paar) and heated at the rate of 1 degree/1 minute. The rheology property was observed at 15° C. to 45° C. As shown in FIG. 2, all five groups formed gels above 25° C. Moreover, gel-forming temperature decreased as buffer concentration increased.

TABLE 5

| Formulation | 20% DP01 (μL) | 20% TP02 (μL) | TBS (μL) | 6x TBS (μL) |
|---|---|---|---|---|
| 15% DP01TP02(5/5) | 375 | 375 | 250 | 0 |
| 15% DP01TP02(5/5)$_{1.5x}$ | 375 | 375 | 150 | 100 |
| 15% DP01TP02(4/6) | 300 | 450 | 250 | 0 |
| 15% DP01TP02(4/6)$_{1.5x}$ | 300 | 450 | 150 | 100 |
| 15% DP01TP02(4/6)$_{2.0x}$ | 300 | 450 | 50 | 200 |

In-Vitro Release Profile

Figure 3:
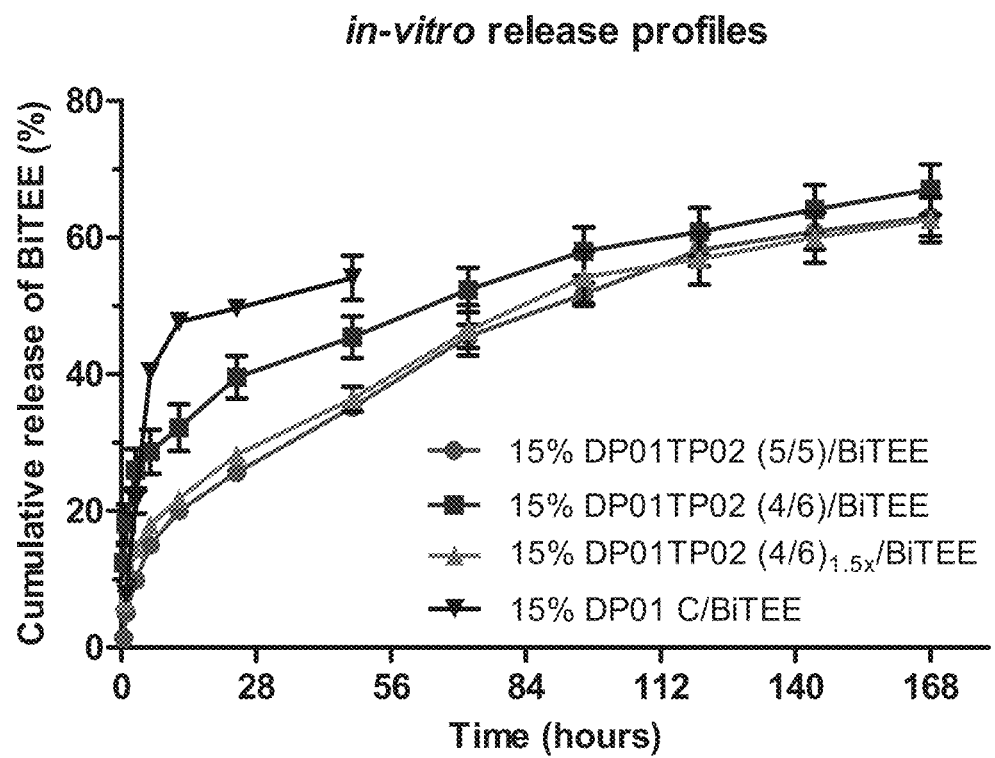
FIG. 3 is a graphic representation of in-vitro release studies for BiTEE loaded hydrogel composition of present disclosure.

Each of 20 μL of 15% DP01TP02(5/5), 15% DP01TP02 (4/6), and 15% DP01TP02(4/6)$_{1.5x}$ loaded 0.5 mg/mL of antibody (anti-EGFR Fab/anti-CD3scFv, BiTEE) was incubated at 37±0.1° C. for 10 minutes. To the mixtures were added 200 μL of release buffer at 37±0.1° C. and 100 rpm. The release buffer was collected and the same volume of release buffer was replenished to maintain the sink condition. Each set of triplicate samples was collected and stored at −80° C. and the levels of antibody were analyzed in an ELISA assay. As shown in FIG. 3, due to the low shrinkage rate, the high water content in the hydrogel can release antibodies steadily, while 15% DP01 demonstrates rapid release.

In-Vivo Pharmacokinetics Studies

Figure 4:
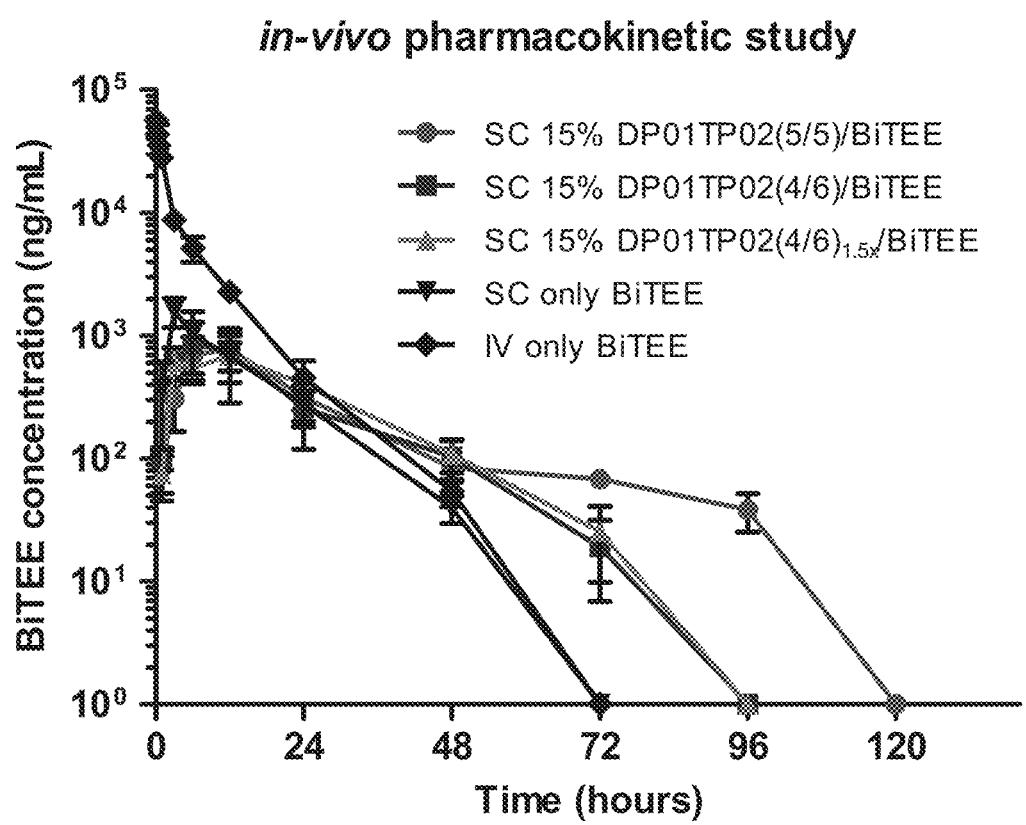
FIG. 4 is a graphic representation of in-vivo pharmacokinetics studies for subcutaneous injection of BiTEE loaded hydrogel composition of present disclosure.

Each of 200 μL of 15% DP01TP02(5/5)/BiTEE, 15% DP01TP02(4/6)/BiTEE and 15% DP01TP02(4/6)$_{1.5x}$/BiTEE with 5 mg/kg BiTEE was injected subcutaneously in the right flank of Balb/c male mice using 26 G needles. Gel-free BiTEE was also injected subcutaneously and intravenously as control groups. Triplicate experiments were performed. The plasma was immediately separated by centrifugation at 6000 rpm for 5 min. Plasma samples were frozen and maintained at −80° C. for analysis. The levels of antibody were analyzed in an ELISA assay. As shown in FIG. 4, the blood concentration can be maintained for at least 96 hours in the 15% DP01TP02(5/5)/BiTEE group, 72 hours in the 15% DP01TP02(4/6)/BiTEE and 15% DP01TP02(4/6)$_{1.5x}$/BiTEE groups and only 48 hours in the control groups.

Effect on Tumor Treatment In Vivo

Figure 5A:
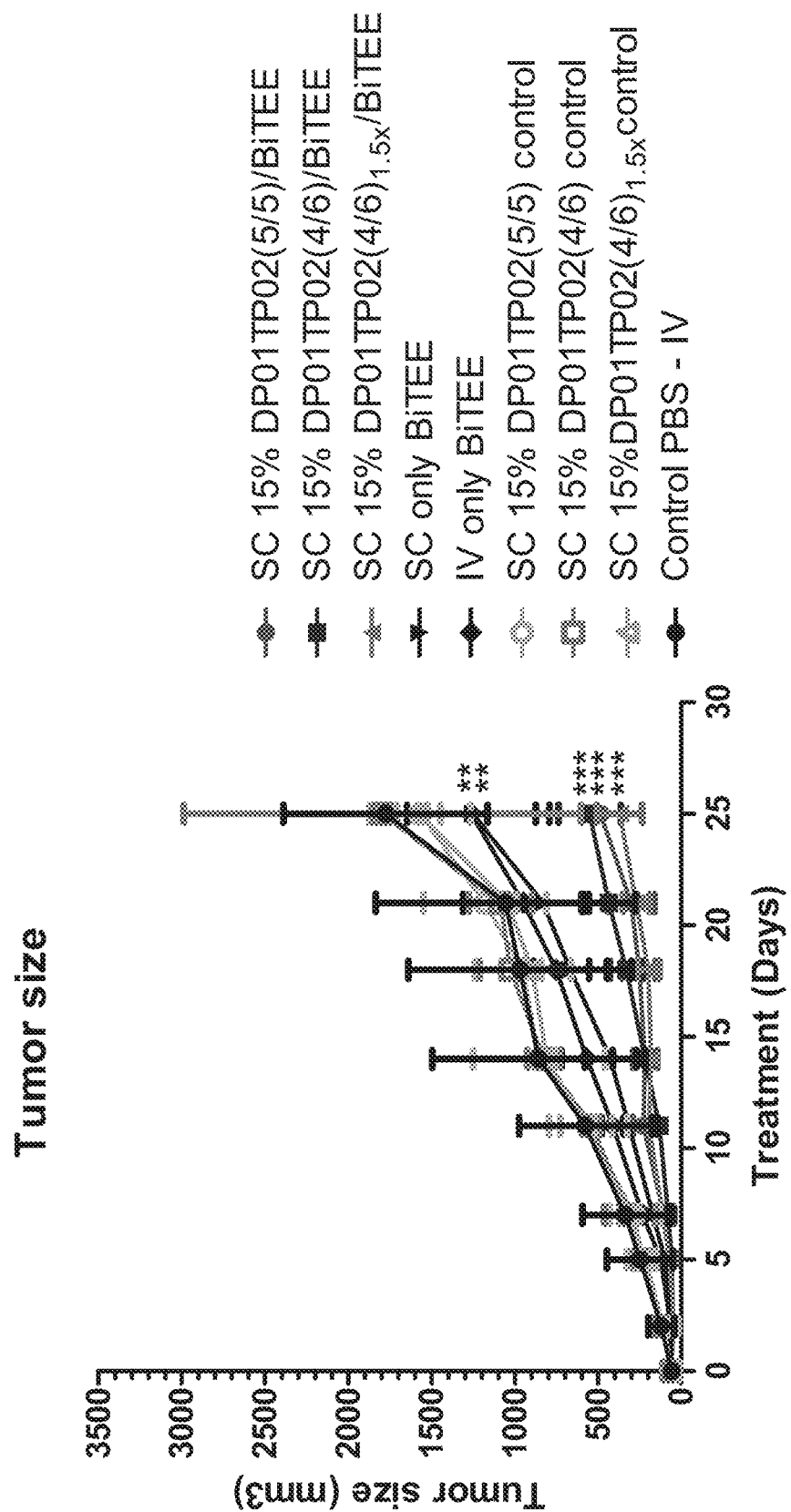
FIG. 5 is a graphic representation of therapeutic efficacy (5A) and toxicity (5B) for subcutaneous injection of BiTEE loaded hydrogel composition of present disclosure.
Figure 5B:
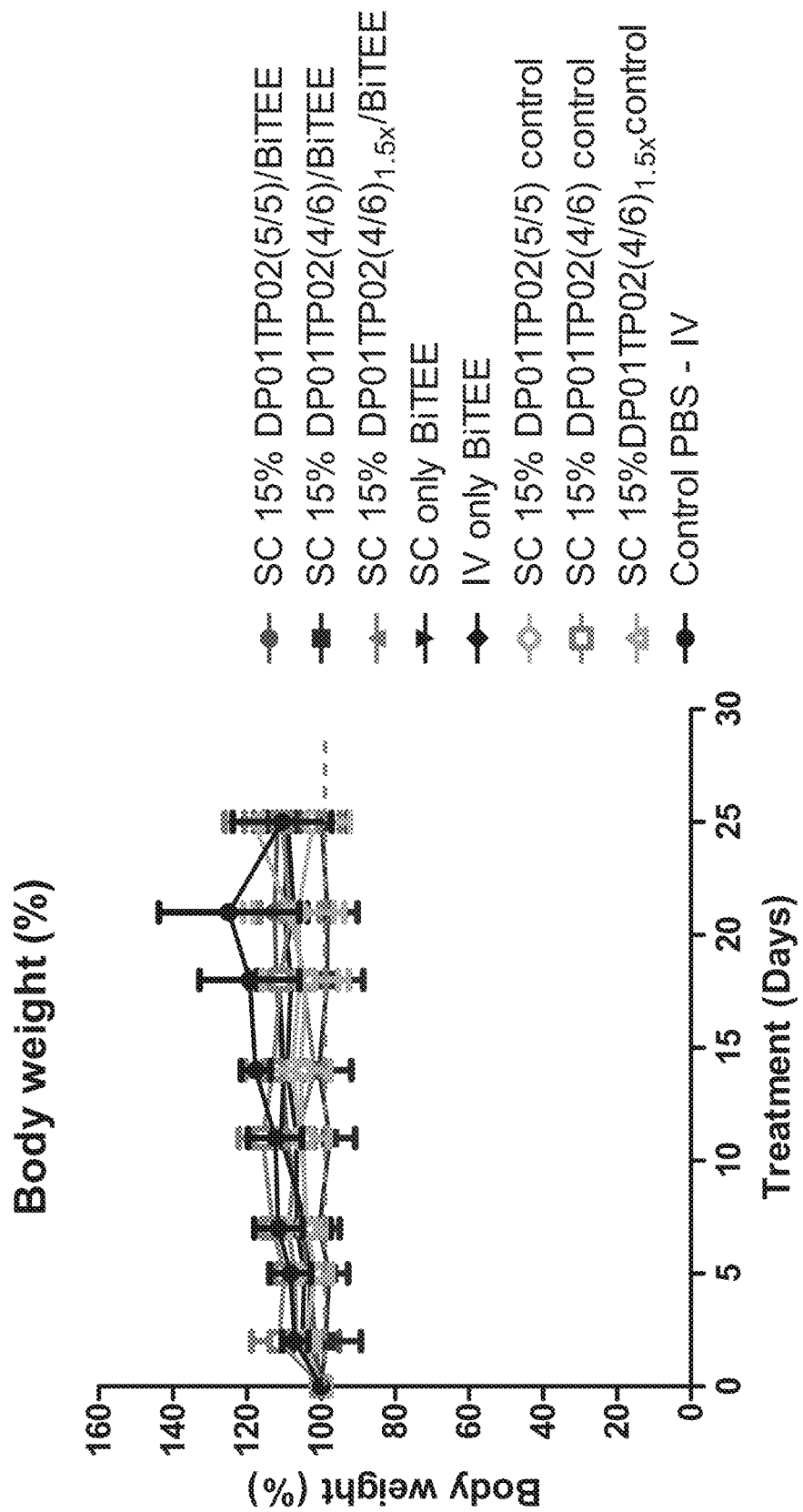
Figure 6A:
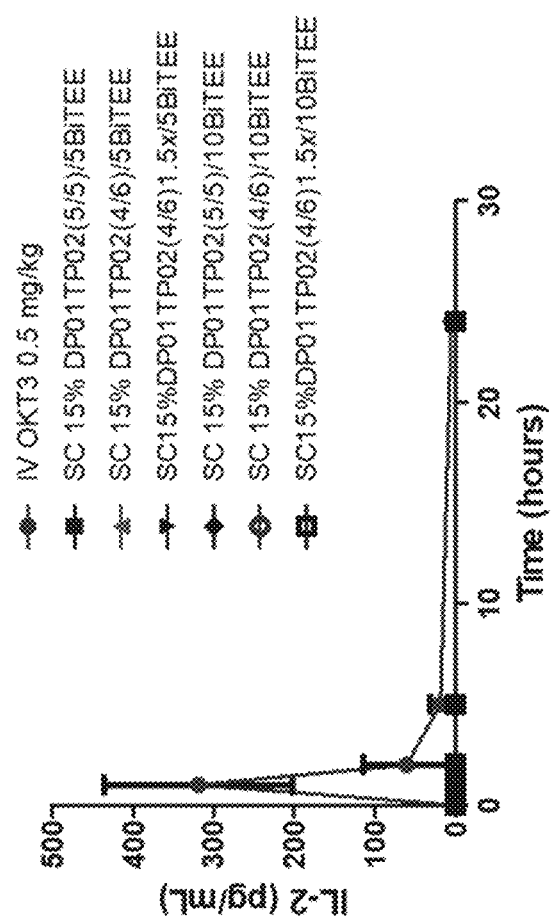
FIG. 6 is a graphic representation of plasma concentration of IL-2 (6A), TNF-α (6B), and IFN-γ (6C) in toxicity study.
Figure 6A:
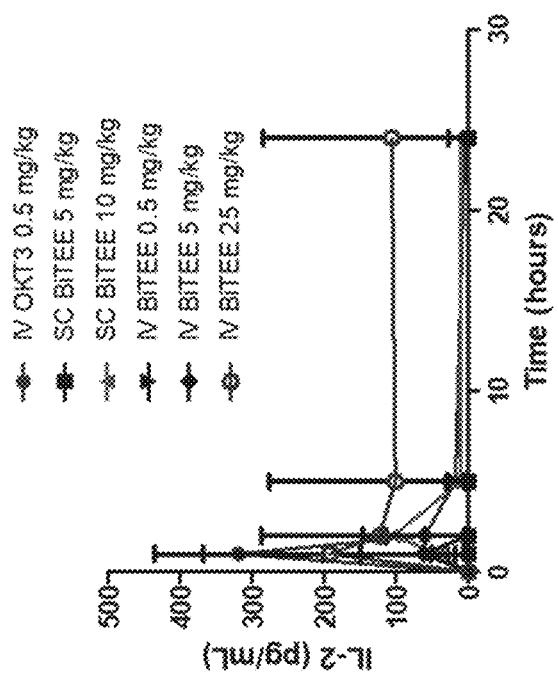
Figure 6B:
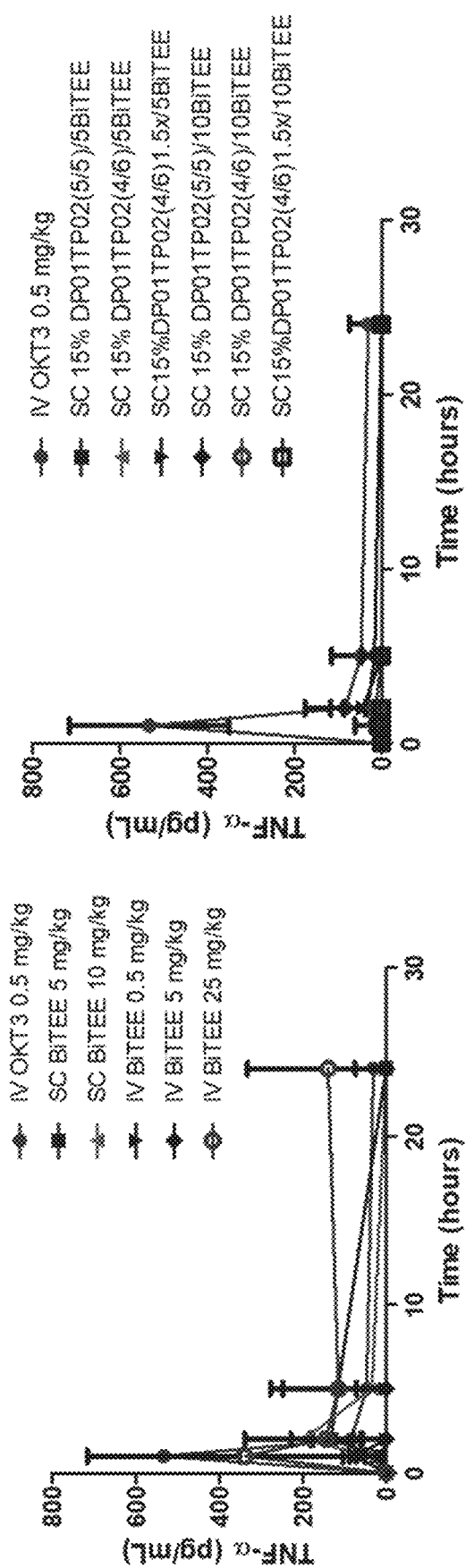

Each of 15% DP01TP02(5/5)/BiTEE, 15% DP01TP02(4/6)/BiTEE and 15% DP01TP02(4/6)$_{1.5x}$/BiTEE with 5 mg/kg BiTEE was injected subcutaneously in the MDA-MB-231 SCID mice. Gel-free BiTEE was also injected subcutaneously or intravenously, or 15% DP01TP02(5/5), 15% DP01TP02(4/6) or 15% DP01TP02(4/6)$_{1.5x}$ was injected subcutaneously, as control groups. Tumor size and body weight of mice were observed twice weekly after injection in order to analyze the effect on tumor treatment in vivo of BiTEE carried by the hydrogel. As shown in FIG. 5A, the groups of 15% DP01TP02(5/5)/BiTEE, 15% DP01TP02(4/6)/BiTEE and 15% DP01TP02(4/6)$_{1.5x}$/BiTEE were all able to inhibit the MDA-MB-231 tumor growth in the SCID mice, and the tumor sizes in these groups were significantly less than those of the control groups of subcutaneously and intravenously injecting BiTEE. As shown in FIG. 6B, There was no significant difference in body weight changes in mice in each group, indicating that 15% DP01TP02(5/5)/BiTEE, 15% DP01TP02(4/6)/BiTEE and 15% DP01TP02(4/6)$_{1.5x}$/BiTEE do not show significant toxicity.

In-Vivo Toxicity Study

Figure 6C:
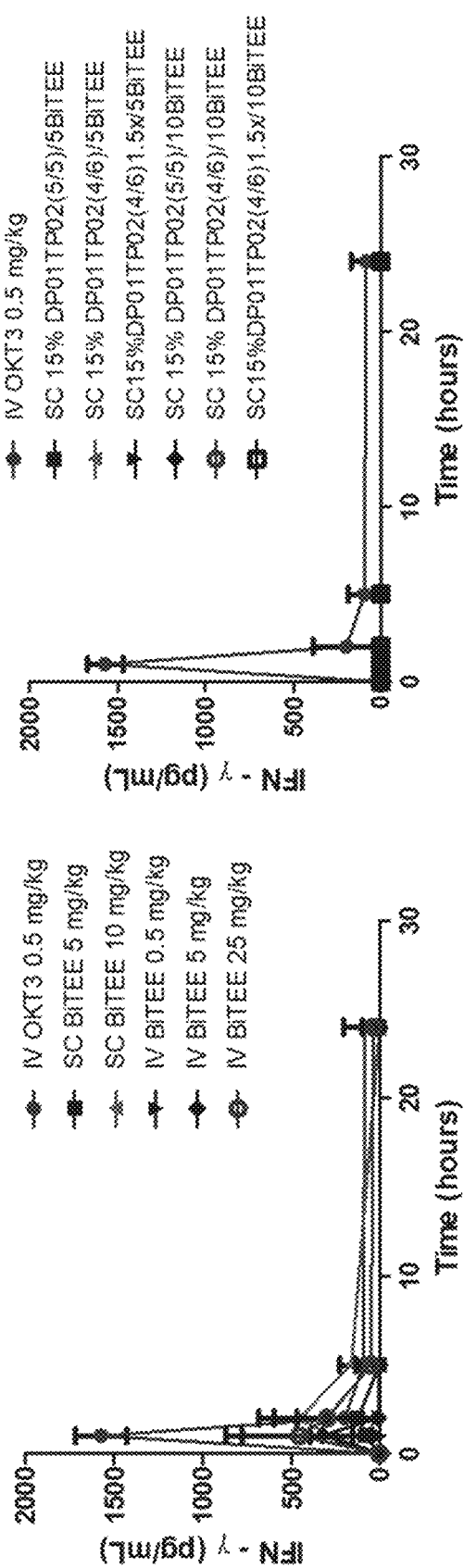

Each of 200 μL of 15% DP01TP02(5/5)/BiTEE, 15% DP01TP02(4/6)/BiTEE and 15% DP01TP02(4/6)$_{1.5x}$/BiTEE with 5 mg/kg BiTEE or 10 mg/kg BiTEE was injected subcutaneously in the right flank of SCID male mice using 26 G needles. In addition, gel-free BiTEE was also injected subcutaneously or intravenously with different dosage and 0.5 mg/kg OKT3 was used as the positive control to measure the cytokines which are related to cytokine release syndrome including IL-2, TNF-α and IFN-γ. Each group was determined in triplicate, and the plasma was immediately separated by centrifugation at 6000 rpm for 5 min. Plasma samples were frozen and maintained at −80° C. until being analyzed. The levels of cytokines were analyzed in an ELISA assay. The plasma concentrations of IL-2, TNF-α and IFN-γ respectively shown in FIGS. 6A, 6B and 6C, were higher in the intravenously group, meaning that the hydrogel formulation shows less toxicity.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. A composition comprising a hydrogel and an active agent, the hydrogel containing:
    a diblock PLGA-PEG copolymer comprising a polyethylene glycol (PEG) segment and a polylactide-co-glycolide (PLGA) segment, the PEG segment having a weight averaged molecular weight ($_w$MW) of from about 400 Da to about 1,000 Da, the PLGA segment having a $_w$MW of from about 900 Da to about 1,800 Da, wherein the ratio of the PEG segment to the PLGA segment is from about 1/1.5 to about 1/3.0, and a total $_w$MW of the diblock PLGA-PEG copolymer is from about 1,000 Da to about 3,000;
    a triblock PLGA-PEG-PLGA copolymer comprising a PEG segment and a PLGA segment, the PEG segment having a $_w$MW of about 800 Da to about 1,600 Da, the PLGA segment having a $_w$MW of about 1,000 Da to about 1,500 Da, wherein the ratio of the PEG segment to the PLGA segment is from about 1/1.5 to about 1/3.0, and a total $_w$MW of the triblock PLGA-PEG-PLGA copolymer is from about 3,000 Da to about 5,000 Da; and
    wherein the ratio of the diblock PLGA-PEG copolymer to the triblock PLGA-PEG-PLGA copolymer is from about 1/9 to about 9/1; and
    the active agent comprising a bispecific T cell/Tumor associated antigen engager (BiTTAE).

2. The composition according to claim 1, wherein the polyethylene glycol segment is a methoxy polyethylene glycol segment.

3. The composition according to claim 1, wherein the diblock PLGA-PEG copolymer comprises the PEG segment having a $_wMW$ of from about 400 Da to about 900 Da, the PLGA segment having a $_wMW$ of from about 900 Da to about 1,800 Da, wherein the ratio of the PEG segment to the PLGA segment is from about 1/1.6 to about 1/2.6, and a total $_wMW$ of the diblock PLGA-PEG copolymer is from about 1,300 Da to about 2,500.

4. The composition according to claim 1, wherein the diblock PLGA-PEG copolymer comprises the PEG segment having a $_wMW$ of from about 550 Da to about 750 Da, the PLGA segment having a $_wMW$ of from about 900 Da to about 1,800 Da, wherein the ratio of the PEG segment to the PLGA segment is from about 1/1.6 to about 1/2.6, and a total $_wMW$ of the diblock PLGA-PEG copolymer is from about 1,300 Da to about 2,500.

5. The composition according to claim 1, wherein the diblock PLGA-PEG copolymer comprises the PEG segment having a $_wMW$ of about 550 Da and the PLGA segment having a $_wMW$ of about 1,400 Da, the ratio of the PEG segment to the PLGA segment is from about 1/2.6, and a total $_wMW$ of the diblock PLGA-PEG copolymer is about 2,000 Da.

6. The composition according to claim 1, wherein the triblock PLGA-PEG-PLGA copolymer comprises the PEG segment having a $_wMW$ of from about 800 Da to about 1,600 Da, the PLGA segment having a $_wMW$ of from about 1,200 Da to about 1,400 Da, wherein the ratio of the PEG segment to the PLGA segment is from about 1/1.6 to about 1/2.6, and a total $_wMW$ of the triblock PLGA-PEG-PLGA copolymer is from about 3,500 Da to about 4,500.

7. The composition according to claim 1, wherein the triblock PLGA-PEG-PLGA copolymer comprises the PEG segment having a $_wMW$ of from about 1,000 Da to about 1,500 Da, the PLGA segment having a $_wMW$ of from about 1,200 Da to about 1,400 Da, wherein the ratio of the PEG segment to the PLGA segment is from about 1/1.6 to about 1/2.6, and a total $_wMW$ of the triblock PLGA-PEG-PLGA copolymer is from about 3,500 Da to about 4,500.

8. The composition according to claim 1, wherein the triblock PLGA-PEG-PLGA copolymer comprises the PEG segment having a $_wMW$ of about 1,500 Da and the PLGA segment having a $_wMW$ of about 1,450 Da, the ratio of the PEG segment to the PLGA segment is from about 1/1.6, and a total $_wMW$ of the triblock PLGA-PEG-PLGA copolymer is about 4,400 Da.

9. The composition according to claim 1, wherein the ratio of the diblock PLGA-PEG copolymer to the triblock PLGA-PEG-PLGA copolymer is from about 1/2 to about 2/1.

10. The composition according to claim 1, wherein the ratio of the diblock PLGA-PEG copolymer to the triblock PLGA-PEG-PLGA copolymer is from about 4/6 to about 6/4.

11. The composition according to claim 1, wherein a sol-gel transition temperature of the hydrogel is from about 25° C. to about 35° C.

12. The composition according to claim 1, which further comprises a salt selected from the group consisting of about 0.137 M to about 0.450 M of NaCl, about 0.0027 M to about 0.0081 M of KCl, about 0.01 M to about 0.03 M of $Na_2HPO_4$, and about 0.0018 M to about 0.0054 M of $KH_2PO_4$.

13. The composition according to claim 1, which further comprises a stabilizer.

14. The composition according to claim 13, wherein the stabilizer is selected from the group consisting of citric acid, lysine monohydrochloride, Tween 80, and trehalose dihydrate.

15. The composition according to claim 1, which comprises about 10 wt % to about 20 wt % of the hydrogel.

16. The composition according to claim 1, wherein the BiTTAE comprises a first antigen-binding domain that binds CD3, a second antigen-binding domain that binds human cancer with over-expressing tumor associated antigen, and wherein a molecular weight of the BiTTAE is from about 50 kDa to about 100 kDa.

17. The composition according to claim 1, wherein the tumor associated antigen in the BiTTAE is EGFR, PSMA, HER2, or EpCam.

18. The composition according to claim 16, wherein the second antigen-binding domain is a construct of tandem scFvs, single chain and tandem diabodies (diabody), dual-affinity retargeting molecules (DARTs), or Fab-scFv.

19. A method for treating or alleviating tumor-of a disease in a subject, comprising administering to the subject the composition according to claim 1 to the subject in need thereof.

20. A method for delivering an active agent comprising using the composition according to claim 1.

21. The method according to claim 20, wherein the bispecific T cell/Tumor associated antigen engager (BiTTAE) comprises a first antigen-binding domain that binds CD3, a second antigen-binding domain that binds human cancer with over-expressing tumor associated antigen, and wherein a molecular weight of the BiTTAE is from about 50 kDa to about 100 kDa.

22. The method according to claim 20, wherein the tumor associated antigen in the BiTTAE is EGFR, PSMA, HER2, or EpCam.

23. The method according to claim 21, wherein the second antigen-binding domain is a construct of tandem scFvs, single chain and tandem diabodies (diabody), dual-affinity retargeting molecules, or Fab-scFv.

24. The method according to claim 20, further comprising administering the hydrogel to a subject in need thereof, wherein the step is selected from the group consisting of: intratumoral injection, subcutaneous injection, peritumoral injection, injection of a resultant cavity of tumor resection, oral delivery, ocular delivery, transdermal, ophthalmic, wound healing, intraperitoneal injection, gene delivery, tissue engineering, colon specific drug delivery.

* * * * *